US00PP37561P3

(12) United States Plant Patent
Neu

(10) Patent No.: US PP37,561 P3
(45) Date of Patent: Aug. 4, 2026

(54) ***PELARGONIUM* PLANT NAMED 'KLEPZ23783'**

(50) Latin Name: ***Pelargonium zonale* x *peltatum***
Varietal Denomination: KLEPZ23783

(71) Applicant: KLEMM + SOHN GMBH & CO. KG, Stuttgart (DE)

(72) Inventor: Nina Neu, Weissach im Tal (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/187,631

(22) Filed: Apr. 23, 2025

(65) Prior Publication Data

US 2026/0123562 P1 Apr. 30, 2026

(30) Foreign Application Priority Data

May 13, 2024 (CH) ..... 24-3627

(51) Int. Cl.
*A01H 5/02* (2018.01)
*A01H 6/42* (2018.01)

(52) U.S. Cl.
USPC ..... Plt./330
CPC ..... *A01H 6/425* (2018.05); *A01H 5/02* (2013.01)

(58) Field of Classification Search
USPC ..... Plt./330
See application file for complete search history.

(56) References Cited

U.S. PATENT DOCUMENTS

PP30,459 P3 4/2019 Klemm et al.

OTHER PUBLICATIONS

CPVO (https://online.plantvarieties.eu/publicConsultationDetails/?registerId=20241379&denomination=KLEPZ23783) retrieved online Jun. 10, 2025 (Year: 2023).*

* cited by examiner

*Primary Examiner* — Susan McCormick Ewoldt
*Assistant Examiner* — Zachariah Allan Kay
(74) *Attorney, Agent, or Firm* — Weatherly IP Solutions, LLC; Karen P. Bechtold; James M. Weatherly

(57) ABSTRACT

A new *Pelargonium* plant particularly distinguished by purple pink flower color with large red spots on the petals, is disclosed.

1 Drawing Sheet

Genus and species: *Pelargonium zonale* x *peltatum*.
Variety denomination: 'KLEPZ23783'.

CROSS REFERENCE TO RELATED APPLICATION

This patent application claims the benefit of priority from Plant Variety Protection Certificate No. 24-3627 as filed on May 13, 2024, in Switzerland, the contents of which are incorporated herein by reference for all it teaches and discloses.

BACKGROUND OF THE NEW PLANT

The present invention comprises a new and distinct variety of *Pelargonium*, botanically known as *Pelargonium zonale* x *peltatum* and hereinafter referred to by the variety name 'KLEPZ23783'. 'KLEPZ23783' originated from a controlled cross in July 2018 in Juja, Kenya between the female *Pelargonium* variety 'KLEPZ12321' (unpatented) and the male *Pelargonium* variety 'KLEPZ17487' (U.S. Plant Pat. No. 30,459).

Seeds from the controlled cross were obtained. The seeds were sown and plants were grown for evaluation. A single plant was selected in June 2019 and subsequently named 'KLEPZ23783'. In July 2019 'KLEPZ23783' was first vegetatively propagated by vegetative stem cuttings in Stuttgart, Germany. 'KLEPZ23783' was found to reproduce true to type in successive generations of asexual propagation via stem cuttings in Stuttgart, Germany.

SUMMARY

The following are the most outstanding and distinguishing characteristics of this new variety when grown under normal horticultural practices in Stuttgart, Germany.

1. Purple pink flower color with large red spots on the petals.

DESCRIPTION OF THE PHOTOGRAPH

This new *Pelargonium* plant is illustrated by the accompanying photograph which shows an overall view of the plant in a pot. The photograph is of an approximately 14-week-old plant grown indoors in Stuttgart, Germany. The photograph was taken indoors in Stuttgart, Germany in May 2022. The colors shown are as true as can be reasonably obtained by conventional photographic procedures.

DESCRIPTION OF THE NEW VARIETY

The following detailed descriptions set forth the distinctive characteristics of 'KLEPZ23783'. Data was collected on 12-week-old plants in Stuttgart, Germany under greenhouse conditions in March 2025. Color references are to The R.H.S. Colour Chart of The Royal Horticultural Society of London (R.H.S.), 5th edition (2007).

Classification:

*Family*.—Geraniaceae.

*Botanical*.—*Pelargonium zonale* x *peltatum*.

*Common*:.—*Pelargonium*.

*Designation*.—'KLEPZ23783'.

Parentage:

*Female parent*.—'KLEPZ12321' (unpatented).

*Male parent*.—'KLEPZ17487' (U.S. Plant Pat. No. 30,459).

Plant:

*Form*.—Bushy.

*Habit*.—Mounding.

*Height* (*from top of soil*).—13 cm.

*Width* (*horizontal plant diameter*).—21 cm.

*Natural flowering season*.—March to October.

*Propagation type*.—Vegetative by stem cuttings.

*Time to produce a finished flowering plant*.—12 weeks.

*Time to initiate and develop roots*.—4 weeks.

*Root description*.—Fine, dense, white, RHS 158A.

*Flower type*.—Zygomorphic.

Stems:

*Quantity of stems per plant*.—5.

*Color*.—RHS 144A.

*Surface texture*.—Pubescent.

*Stem form*.—Round.

*Diameter*.—0.8 cm.

*Length*.—6 to 8 cm.

*Internode length*.—1.0 cm.

*Anthocyanin*.—None.

Leaves:

*Arrangement*.—Alternate.

*Shape*.—Reniform.

*Apex*.—Round.

*Base*.—Open.

*Margin*.—Crenate.

*Surface texture both surfaces*.—Both pubescent.

*Length*.—7.5 cm.

*Width*.—9.5 cm.

*Color*.—Upper surface: RHS 137A. Lower surface: RHS 137C.

*Zonation*.—None.

*Depth of sinus*.—2.3 cm.

*Petiole*.—Length: 4.5 cm. Diameter: 0.3 cm. Color: RHS 144A.

*Venation pattern*.—Palmate.

*Venation color*.—Upper surface: RHS 137A. Lower surface: RHS 144A.

Inflorescence:

*Lastingness of flowers on the plant*.—6 to 8 days.

*Umbels*.—Quantity of umbels per plant.—5 to 7. Length.—5.0 cm. Diameter.—8.0 cm.

*Individual florets of the umbel*.—Quantity of flowers per umbel: 10 to 13. Depth: 2.0 cm. Diameter: 4.5 cm.

*Fragrance*.—Absent.

Flower buds:

*Cluster shape*.—Round.

*Cluster size*.—Length: 2.0 cm. Width: 1.5 cm.

*Surface texture*.—Pubescent.

*Bud*.—Height: 1.5 cm. Width: 0.5 cm. Shape: Elliptic. Apex: Acute. Base: Obtuse. Margin: Entire. Color: RHS 144A.

Petals:

*Quantity per flower*.—5.

*Shape*.—Spatulate.

*Apex*.—Round.

*Base*.—Obtuse.

*Margin*.—Entire.

*Length*.—2.9 cm.

*Width*.—2.8 cm.

*Surface texture*.—Upper surface: Smooth. Lower surface: Smooth.

*Color of lobes*.—Upper lobes: Upper surface: RHS N74A basic color, RHS 46B marking. Lower surface: RHS N74B. Lower lobes: Upper surface: RHS N74A basic color, RHS 46B marking. Lower surface: RHS N74B.

*Markings*.—Yes, a large single spot, 0.7 cm in diameter and occupying the central third of the petal.

Petaloids:

*Quantity per flower*.—0 (no filling of flower).

Sepals:

*Number per flower*.—5.

*Shape*.—Elliptic.

*Apex*.—Acute.

*Base*.—Obtuse.

*Margin*.—Entire.

*Surface texture*.—Upper surface: Smooth. Lower surface: Pubescent.

*Color*.—Upper surface: Anthocyanin at base RHS 46B, green tip RHS 144A. Lower surface: Anthocyanin at base RHS 46B, green tip RHS 144A.

*Length*.—1.1 cm.

*Width*.—0.3 cm.

Pedicel:

*Length*.—2.3 cm.

*Diameter*.—0.2 cm.

*Color*.—RHS 184A.

*Surface texture*.—Pubescent.

Peduncle:

*Length*.—7.0 cm.

*Diameter*.—0.3 cm.

*Color*.—RHS 144A.

*Texture*.—Pubescent.

Reproductive organs:

*Stamens*.—Quantity per flower: 5. Anther length: 0.1 cm. Filament length: 0.9 cm. Filament color: RHS N57C at tip, RHS NN155D at base. Pollen amount: Abundant. Pollen color: RHS 42C.

*Pistils*.—Number: 1. Stigma color: RHS 64A. Style length: 0.3 cm. Style color: RHS 64A. Ovary arrangement: Central. Ovary color: RHS 144A. Ovary diameter: 0.1 cm. Ovary length: 0.4 cm. Ovary Texture: Pubescent.

Fruit and seed set: Not observed to date.

Disease and pest/insect resistance: Not observed to date.

COMPARISON WITH PARENTAL LINES AND KNOWN VARIETY

'KLEPZ23783' is distinguished from its parents as described in Table 1.

TABLE 1

Comparison with Parental Lines

| Characteristic | 'KLEPZ23783' | Female parent | Male parent |
|---|---|---|---|
| Flower basic color | Purple pink with red spots | Pink with red spots | White with red spots |

'KLEPZ23783' can be compared to the commercial variety PAC Flower Two in One Hot Pink Splash (patent status unknown). Differences between the two varieties are described in Table 2:

TABLE 2

Comparison with Similar Variety

| Characteristic | 'KLEPZ23783' | 'PAC Flower Two in One Hot Pink Splash' |
|---|---|---|
| Flower color marking size | 0.7 cm in diameter | 0.4 cm in diameter |

I claim:

1. A new and distinct variety of *Pelargonium* Plant Named 'KLEPZ23783' as illustrated and described herein.

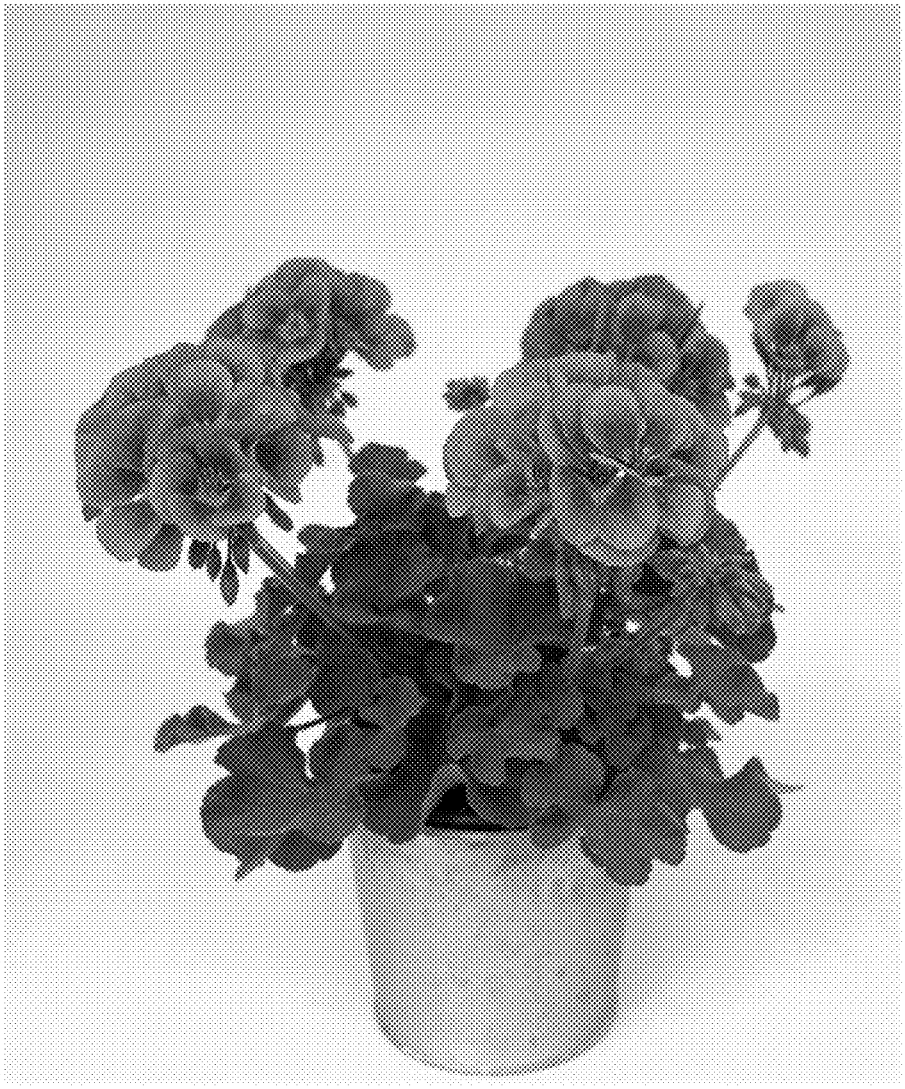

* * * * *